Oct. 8, 1974 | C. G. KLEHM | Plant Pat. 3,636
PEONY PLANT
Filed Oct. 26, 1973
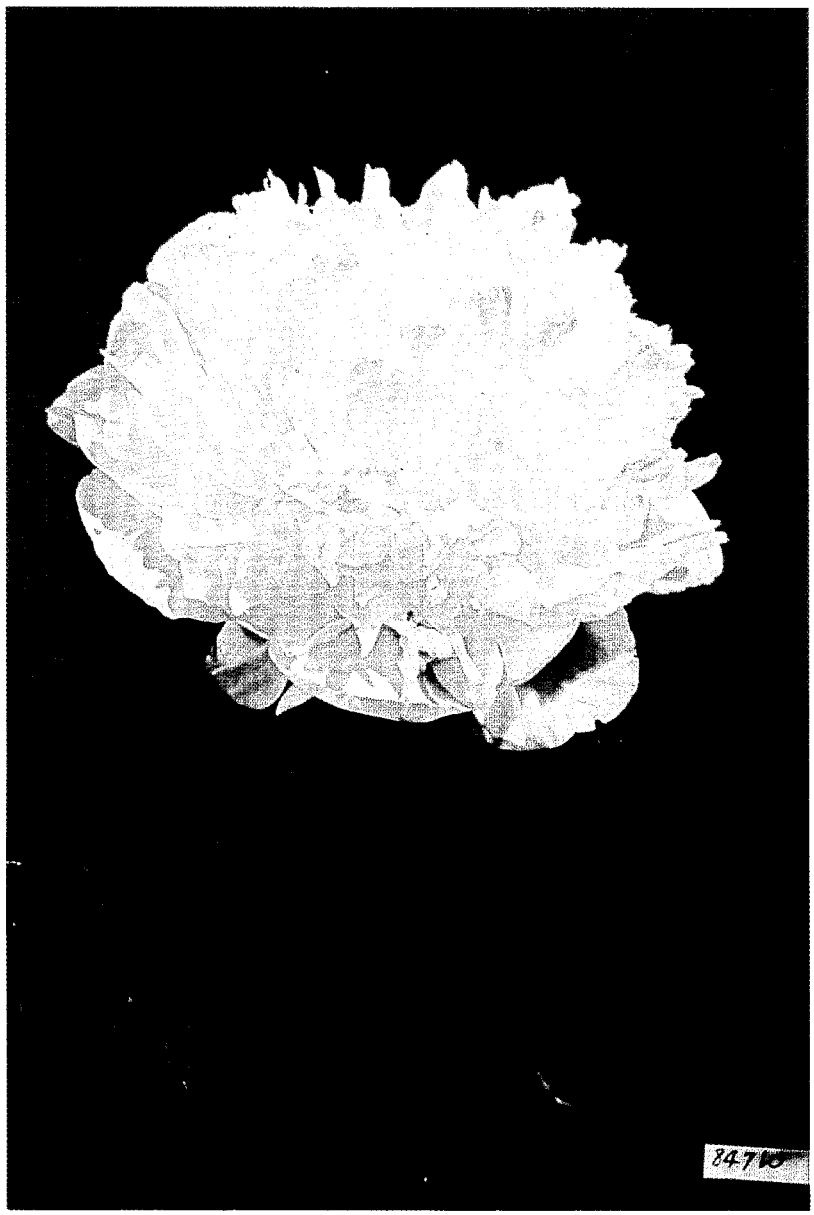

United States Patent Office

Plant Pat. 3,636
Patented Oct. 8, 1974

3,636
PEONY PLANT

Carl George Klehm, Arlington Heights, Ill., assignor to Klehm Properties, Inc., Arlington Heights, Ill.

Filed Oct. 26, 1973, Ser. No. 410,208
Int. Cl. A01h 5/00
U.S. Cl. Plt.—68 1 Claim

ABSTRACT OF THE DISCLOSURE

A new variety of peony plant characterized by a strong and tall growth habit and its profuse production of very large, fully double, generally white rose type blooms which are particularly distinguished by the large amount of sulphur yellow color showing throughout the flower from many yellow petaloids and some yellow petals interspersed among many relatively large pure white petals, the white and yellow flower body being cupped by a surrounding array of large pure white guard petals.

BACKGROUND OF THE NEW PLANT

This new peony plant originated as a seedling produced by my crossing of the unpatented variety Mons. Jules Elie with an unnamed and unpatented "bull" hybrid, identified in my records as 71D, maintained in my breeding stock to be used exclusively for hybridizing. Mons. Jules Elie is the seed parent of this new plant and the crossing was done by me at Arlington Heights, Ill., in the course of extensive breeding efforts carried on by me since 1945 with the object of developing new, improved and distinctive peony varieties. This plant was selected by me for propagation and testing from among several outstanding seedlings resulting from my breeding program because of the unique white and yellow coloration of the blossoms and its remarkably strong and vigorous growth habit.

Asexual propagation of this new plant by root division has been done by me and under my direction since 1951 at Arlington Heights, Ill., and continuous observation of these plants through many generations has shown that the novel and distinctive features of the original seedling are firmly established and come true to form from generation to generation. Propagation of this new plant by root division and on a commercial scale is now being carried on in nurseries at Arlington Heights, Barrington and Champaign, Ill.

Description of the Drawing

This new variety of poeny plant is illustrated by the accompanying full color photographic drawing which shows the flower in full bloom and some of the foliage, the color rendition of the flower being as nearly true as it is reasonably possible to obtain by conventional professional photographic procedures.

Description of the New Plant

The following is a detailed description of my new variety of peony plant with color specification according to The RHS Colour Chart produced with collaboration of the British Colour Council and published by The Royal Horticultural Society at London, England.

THE PLANT

Origin: Seedling.
Parentage:
*Seed Parent*—Mons. Jules Elie (unpatented).
*Pollen Parent*—71D (An unnamed and unpatented "bull" hybrid used exclusively for hybridizing).
Classification: Botanic—*Paeonia lactiflora.*
Form: Bush of generally round shape.

Height: 35 to 40 inches.
Growth: Vigorous, strong and upright.
Foliage: Quantity—Abundant with 6 to 9 leaves per stem.
*Shape of Leaf*: Elliptically acute with smooth margins.
*Size of Leaf*: 14 to 16 inches long.
*Aspect*: Glossy.
*Leaflets*: Three in number. Size: 10 to 11 inches long.
*Petioles*: 2 to 3 inches long.
*Rachis*: 1½ to 2 inches long.
*Ribs and Veins*: Extremely pronounced.

THE BUD

Size: Medium large.
*Diameter*: About 1 17/64 to 1⅜ inches.
*Depth*: 1 inch.
Form: Ovoid.
Opening Rate: Average.
Sepals: Hooded over the bud.
Calyx: Shape—Funnel.
*Size*: Large.
*Aspect*: Smooth.
Splitting: Calyx does not split.

THE FLOWER

Blooming Habit: Once, profusely, in early Summer (June in Arlington Heights, Ill.).
Size: Very large.
*Diameter*: 8 to 8½ inches.
Shape: Cup-shaped when bloom first opens, changing to fully double, rose type as flower matures.
Borne: Singly. One terminal flower with two to four auxiliary buds on each main stem.
Petalage: Heavy and extremely double.
*Arrangement*: Imbricated with two or three rows of slightly notched guard petals.
*Color*: Outer petals—White. Inner petals—Mostly White—some Yellow, Yellow Group 7–C.
*Texture*: Soft.
*Appearance*: Satiny.
Petaloids: Many—¼ to 1¾ inches long.
*Color*: Medium Yellow, Yellow Group 7–C.

REPRODUCTIVE ORGANS

Stamens: Very few anthers on filaments, about ¼ inch long. Color—Dark Yellow.
*Pollen*: Deep Yellow in color.
Pistils: None.

The distinguishing feature of this new variety of peony plant is the flower which has a large amount of sulphur yellow color showing throughout a large central mass of white petals, the flower being very large in size and of a full double rose type form with large pure white guard petals. This combination results in a unique and outstanding peony blossom and coupled with large and luxuriant foliage and strong, tall growth habit of the plant, this plant is a distinctive addition to the art of peony culture.

I claim:

1. A new and distinct variety of peony plant substantially as herein shown and described, characterized in particularly by the very large size of its generally white, full double, rose type flower form and the large number of yellow petaloids interspersed among the white petals to provide a large amount of yellow color showing throughout the white of the blossom body.

No references cited.

ROBERT E. BAGWILL, Primary Examiner